United States Patent [19]

Motegi et al.

[11] Patent Number: 5,115,069
[45] Date of Patent: May 19, 1992

[54] GLYCIDOXY GROUP-CONTAINING ORGANOSILICON COMPOUND

[75] Inventors: Hisao Motegi; Takeshi Sunaga; Michio Zenbayashi, all of Gunma, Japan

[73] Assignee: Toshiba Silicone Co., Ltd., Tokyo, Japan

[21] Appl. No.: 499,740

[22] Filed: Mar. 27, 1990

[30] Foreign Application Priority Data

Mar. 29, 1989 [JP] Japan .................................. 1-76913

[51] Int. Cl.$^5$ .............................................. C08G 77/06
[52] U.S. Cl. ...................................... 52.8/15; 528/27; 549/215
[58] Field of Search .................... 549/215; 528/27, 15

[56] References Cited

U.S. PATENT DOCUMENTS

| | | | |
|---|---|---|---|
| 4,208,503 | 6/1980 | Martin | 549/215 |
| 4,689,383 | 8/1987 | Riffle et al. | 528/12 |
| 4,987,203 | 1/1991 | Saho et al. | 528/15 |

FOREIGN PATENT DOCUMENTS

| | | |
|---|---|---|
| 0294525 | 6/1987 | European Pat. Off. |
| 0269114 | 11/1987 | European Pat. Off. |
| 8343526 | 5/1960 | United Kingdom |

*Primary Examiner*—Melvyn I. Marquis
*Attorney, Agent, or Firm*—Sughrue, Mion, Zinn, Macpeak & Seas

[57] ABSTRACT

A glycidoxy group-containing organosilicon compound represented by formula (I)

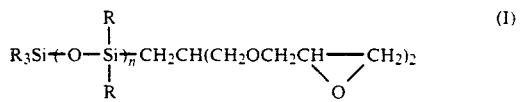

wherein R which may be the same or different each represents an alkyl group, an aryl group, or an alkenyl group, and n is 0 or an integer of 1 to 1,000. The compound is useful for modification of interfacial properties of various synthetic resins such as epoxy resins, polyesters, polyurethanes, polyamides and polyimides.

4 Claims, No Drawings

GLYCIDOXY GROUP-CONTAINING ORGANOSILICON COMPOUND

FIELD OF THE INVENTION

The present invention relates to an organosilicon compound useful for modifying properties of synthetic resins. More particularly, this invention relates to a novel glycidoxy group-containing organosilicon compound useful for the modification of interfacial properties of synthetic resins such as epoxy resins, polyesters, polyurethanes, polyamides, polyimides, and the like produced by utilizing the reactivity of an epoxy group, hydroxyl group, carboxyl group, and amino group.

BACKGROUND OF THE INVENTION

Conventionally known glycidoxy group-containing organosilicon compounds for use in the modification of interfacial properties of epoxy resins, polyesters, polyurethanes, polyamides, or polyimides include compounds of the following formula (II) having an organic group having a glycidoxy group at both ends of a dimethylsiloxane oligomer, and compounds of the following formula (III) having an organic group having one glycidoxy group at one end of a dimethylsiloxane oligomer. The compounds of formulas (II) and (III) are disclosed in, for example, JP-A-62-192423. (The term "JP-A" as used herein means an "unexamined published Japanese patent application".)

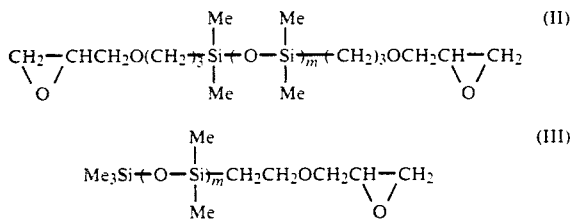

wherein Me represents a methyl group, and m represents a positive integer.

However, modification of a polymer by the compound of formula (II) has a problem that since the whole siloxane segment is introduced into the resulting polymer, the compound (II) should be used in a considerably large proportion for attaining sufficient modification of interfacial properties of the final resin molded articles. In the case of the compound of formula (III), there is a problem that since the compound is not a so-called bifunctional compound, a high molecular weight polymer is difficult to obtain or the compound (III) cannot be used as a crosslinking agent to crosslink organic polymer molecules.

SUMMARY OF THE INVENTION

Accordingly, an object of the present invention is to provide a novel glycidoxy group-containing organosilicon compound which is free from the above problems and useful in the modification of interfacial properties of epoxy resins, polyesters, polyurethanes, polyamides, polyimides, and other resins.

The glycidoxy group-containing organosilicon compound of the present invention is represented by formula (I)

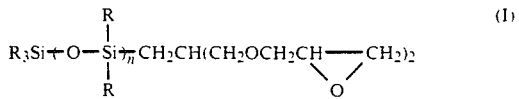

wherein R which may be the same or different each represents an alkyl group, an aryl group, or an alkenyl group, and n is 0 or an integer of 1 to 1,000.

DETAILED DESCRIPTION OF THE INVENTION

The compound of formula (I) is hereinafter referred to as "compound (I)".

In the compound (I) of this invention, R is an alkyl group, an aryl group, or an alkenyl group. Examples of the alkyl group include methyl, ethyl, propyl, butyl, pentyl, hexyl, and dodecyl, examples of the aryl group include phenyl and tolyl, and examples of the alkenyl group include vinyl and allyl. Of these, alkyl groups having 1 to 4 carbon atoms are preferred, with methyl being particularly preferred, from the standpoints of easy availability of raw materials and easy synthesis of the compound.

n is 0 or an integer of 1 to 1,000, preferably 1 to 200. If n is larger than 1,000, not only does the viscosity of the compound becomes so high that the compound is difficult to handle, but synthesis thereof is difficult to control.

One example of a process for producing the compound (I) of the present invention is briefly explained below.

First, 2-methylene-1,3-propanediol (IV) and epichlorohydrin (V) are subjected to an addition reaction in the presence of an acid catalyst to give a chlorohydrin derivative (VI). This derivative is reacted with a basic hydroxide such as sodium hydroxide to eliminate hydrogen chloride from the derivative, thereby to synthesize 2-methylene-1,3-diglycidoxypropane (VII). This compound (VII) is then subjected to a hydrosilylation reaction with a one-end-hydrogenated diorganosiloxane oligomer (VIII) in the presence of a catalyst such as a platinum compound, thereby to obtain the compound (I) of the invention. The above process is illustrated by the following reaction formulas.

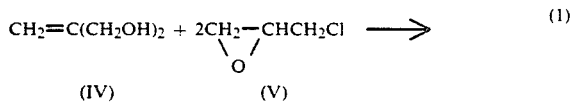

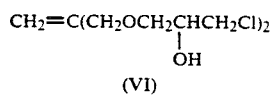

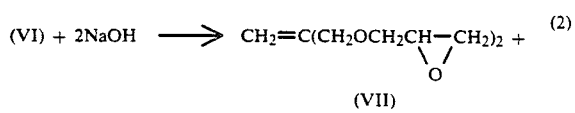

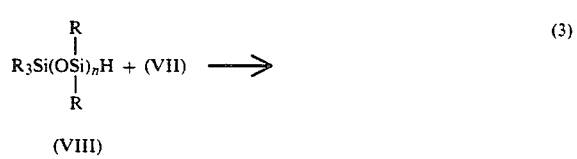

-continued

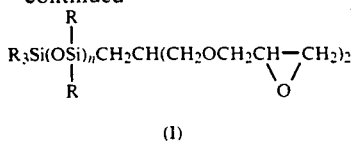

(I)

wherein R and n are the same as defined above.

Compound (IV) can be obtained, for example, by a method in which 5-norbornen-2-ylidene dimethanol is subjected to a retro Diels-Alder reaction (E. J. Corey, J. W. Suggs; Tetrahedron Lett., 44, 3775–3778(1975)) or a method in which 3-chloro-2-chloromethylpropene is esterified with acetic acid to synthesize 2-methylene-1,3-propanediol diacetate, which is then subjected to an ester interchange reaction with methanol (Y. Ducharme, S. Latour, J. D. Wuest; Organometallics, 3, 208–211(1984)).

The one-end-hydrogenated diorganosiloxane oligomer, compound (VIII), can be obtained as follows. A compound of formula (VIII) in which n is 0, i.e., a triorganosilane, can be easily obtained by reacting a triorganochlorosilane of the formula $R_3SiCl$ (wherein R is the same as defined above) with a theoretical molar amount of lithium aluminum hydride in ether. A compound of formula (VIII) in which n is 1, i.e., a 1,1,3,3,3-pentaorganodisiloxane, can be easily obtained, for example, by subjecting a triorganochlorosilane of the formula $R_3SiCl$ (wherein R is the same as defined above) and a diorganochlorosilane of the formula $R_2HSiCl$ (wherein R is the same as defined above) to a cohydrolysis reaction. A compound of formula (VIII) in which n is 2 or larger can be obtained by polymerizing a hexaorganocyclotrisiloxane of the general formula $[R_2SiO]_3$ in tetrahydrofuran in the presence of an organolithium compound of the formula RLi (wherein R is the same as defined above), and then subjecting the resulting polymer to a desalting reaction with a diorganochlorosilane of the formula $R_2HSiCl$ (wherein R is the same as defined above) (for example, Y. Tezuka, A. Fukushima, K. Imai; Makromolekulare Chemie, 186, 685(1985)).

The addition reaction shown by reaction formula (1) can be conducted by adding dropwise a theoretical molar amount or more of compound (V) to a liquid mixture of compound (IV) and an acid catalyst at a temperature of the liquid mixture of 60° to 90° C. Examples of the acid catalyst used for this reaction include sulfuric acid, toluenesulfonic acid, boron trifluoride, and stannic chloride. Of these, stannic chloride is preferably used because of its high catalytic activity.

The hydrogen chloride-elimination reaction shown by reaction formula (2) can be carried out by reacting compound (VI) with a theoretical molar amount or more, preferably 2.2 moles or more, per mole of the compound (VI), of a basic hydroxide. The basic hydroxide is used in a powder form or in the form of a high concentration aqueous solution. Examples of the basic hydroxide used for this reaction include sodium hydroxide, potassium hydroxide, barium hydroxide, and calcium hydroxide. Of these, sodium hydroxide is preferably used because of its easy handling and high reactivity.

In conducting the hydrosilylation reaction of compound (VII) with compound (VIII), as shown by reaction formula (3), the amount of compound (VII) is a theoretical molar amount or more, preferably 1.1 moles or more, per mole of compound (VIII). A catalyst for this hydrosilylation reaction is complex compounds of Group VIII elements in the periodic table. Of these, a platinum compound prepared by dissolving chloroplatinic acid in an alcohol or a carbonyl compound, and complex compounds of various olefins with platinum or rhodium are preferably used. After completion of the reaction, low boiling point ingredients remaining unreacted ar evaporation-removed under reduced pressure and, if desired and necessary, the resulting product is subjected to active carbon treatment etc. to remove the hydrosilylation catalyst or to decolor the product, whereby the compound (I) of this invention can be obtained.

By using the compound of the present invention to modify epoxy resins, polyesters, polyurethanes, polyamides, polyimides, or the like, plastic materials can be obtained which have a structure in which siloxane segments are attached as pendant groups to the polymer backbone.

Due to the compound of the present invention, the plastic materials thus obtained possess excellent interfacial properties such as wear resistance, water repellency, release characteristics, molding properties, and surface-slip characteristics, physical properties such as heat resistance and electrical characteristics, and mechanical properties such as impact resistance, pliability, and low temperature properties. Therefore, the plastic materials obtained by using the compound of this invention are useful as sealing materials for semiconductors, passivation films for semiconductors, and the like.

The present invention will be explained below in more detail by reference to the following Examples, which should not be construed to be limiting the scope of the invention. In the Examples, all parts are by weight.

EXAMPLE 1

Into a flask equipped with a stirrer, thermometer, dropping funnel, reflux condenser, and oil bath were introduced 88 parts of 2-methylene-1,3-propanediol and 6 parts of stannic chloride. Stirring was then initiated and the liquid mixture in the flask was heated to 70° C.

From the dropping funnel, 194 parts of epichlorohydrin was added dropwise to the above mixture over a period of 15 minutes, while appropriately cooling the liquid reaction mixture to maintain the liquid temperature at 70°–90° C. After completion of the addition, stirring was continued for 1 hour at a liquid temperature of 90° C. Upon analysis by gas chromatography, it was ascertained that the peak due to 2-methylene-1,3-propanediol had disappeared and its addition reaction product had been formed.

After the liquid reaction mixture was cooled to 10° C. with an ice bath, a solution prepared by dissolving 96 parts of sodium hydroxide in 120 parts of water was added dropwise to the flask from the dropping funnel over a period of 15 minutes, while the reaction mixture was kept at 10°–15° C. After completion of the addition, the resulting mixture was stirred at room temperature for 2 hours, and 400 parts of n-hexane was added to separate the reaction mixture into an aqueous phase and an organic phase. The organic phase was washed with a saturated NaCl aqueous solution until the organic phase became neutral, and then dried by adding anhydrous sodium sulfate thereto.

From the thus-dried organic phase, a fraction having a boiling point of 129°–131° C./3 Torr was taken by vacuum distillation, thereby obtaining 160 parts of 2-methylene-1,3-diglycidoxypropane in a colorless, transparent liquid state (yield 80%).

0.75 Part of a solution prepared by dissolving 5 parts of chloroplatinic acid in 250 parts of isopropanol and 154 parts of 2-methylene-1,3-diglycidoxypropane were introduced into the same type of a flask as used above. Stirring was then initiated and the liquid mixture was heated to 70° C.

To the above mixture, 104 parts of 1,1,3,3,3-pentamethyldisiloxane was added dropwise from the dropping funnel over a period of 15 minutes, while appropriately cooling the liquid mixture to maintain its temperature at 80°-90° C. After completion of the addition, the resulting liquid mixture was stirred at a liquid temperature of 90° C. for 1 hour. Upon analysis by infrared spectroscopy, it was ascertained that the absorption peak (2,140 cm$^{-1}$) due to Si—H group had disappeared.

After the reaction mixture was allowed to cool, low boiling point ingredients were removed by evaporation at a liquid temperature of 150° C. under reduced pressure of 2 Torr over 2 hours. The thus-obtained liquid distillation residue was cooled to room temperature, and 5 parts of active carbon was added thereto. The resulting mixture was stirred for 1 hour and filtered off, thereby obtaining 236 parts of 1-(2-glycidoxymethyl-3-glycidoxypropyl)-1,1,3,3,3-pentamethyldisiloxane (yield 97%).

The above-obtained product was subjected to gas chromatographic analysis, elementary analysis, infrared spectroscopic analysis, $^1$H nuclear magnetic resonance ($^1$H NMR) analysis, and mass spectrometric analysis. The results obtained are shown below. From those analyses, the product was ascertained to have the following molecular structure.

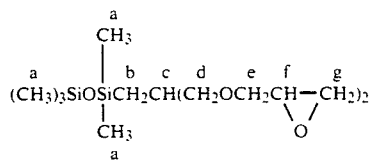

Gas chromatographic analysis:

Purity of the major ingredient 97.1%

Elementary analysis:

Found value Si; 16.12%, C; 51.67%, H; 9.24%, O; 22.97%.

Calculated value Si; 16.11%, C; 51.69%, H; 9.25%, O; 22.95%.

| Infrared spectroscopic analysis (liquid film method): | |
|---|---|
| Wave number (cm$^{-1}$) | Assignment |
| 2950 | C—H |
| 1240 | Si—CH$_3$ |
| 1120-1060 | C—O—C |
| 1070-1040 | Si—O—Si |

| $^1$H NMR analysis (90 MHz, in CDCl$_3$): | | | |
|---|---|---|---|
| Position | Chemical shift δ (ppm) | Integrated intensity | Multiplicity |
| a | −0.02 | 15H | s |
| b | 0.4–0.6 | 2H | d |
| c | 1.8–2.2 | 1H | m |
| d | 3.3–3.5 | 4H | d |
| e | 3.2–3.7 | 4H | m |
| f | 2.9–3.2 | 2H | m |
| g | 2.5–2.8 | 4H | d |

Mass spectrometric analysis (m/e): 348 (M$^+$)

EXAMPLE 2

Reaction was conducted in the same manner as in Example 1 except that 700 parts of a one-end-hydrogenated dimethylsiloxane oligomer (hydrogen equivalent: 2,000, i.e., number average molecular weight: 2,000) was used in place of 1,1,3,3,3-pentamethyldisiloxane used in Example 1, and the amount of 2-methylene-1,3-diglycidoxypropane added was changed to 80 parts. Thus, 747 parts of a one-end-glycidoxy-modified dimethylsiloxane oligomer was obtained in a colorless, transparent liquid state (yield 98%).

The above-obtained oligomer was subjected to infrared spectroscopic analysis, $^1$H NMR analysis, epoxy equivalent determination, and GPC analysis. The results obtained are shown below. From those analyses, the oligomer was ascertained to have the following molecular structure.

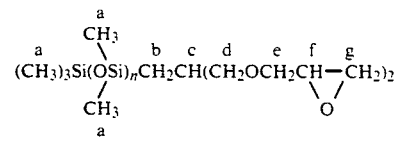

| Infrared spectroscopic analysis (liquid film method): | |
|---|---|
| Wave number (cm$^{-1}$) | Assignment |
| 2950 | C—H |
| 1240 | Si—CH$_3$ |
| 1120-1060 | C—O—C |
| 1070-1040 | Si—O—Si |

| $^1$H NMR analysis (90 MHz, in CDCl$_3$): | | | |
|---|---|---|---|
| Position | Chemical Shift δ (ppm) | Integrated intensity | Multiplicity |
| a | −0.02 | — | s |
| b | 0.4–0.6 | 2H | d |
| c | 1.8–2.2 | 1H | m |
| d | 3.3–3.5 | 4H | d |
| e | 3.2–3.7 | 4H | m |
| f | 2.9–3.2 | 2H | m |
| g | 2.5–2.8 | 4H | d |

Epoxy equivalent determination:

Epoxy equivalent 1,100

GPC analysis:

Weight-average molecular weight expressed in terms of polystyrene (M$_w$) 2,400

Number-average molecular weight expressed in terms of polystyrene (M$_n$) 2,200

Degree of polydispersion (M$_w$/M$_n$) 1.09.

While the invention has been described in detail and with reference to specific embodiments thereof, it will be apparent to one skilled in the art that various changes and modifications can be made therein without departing from the spirit and scope thereof.

What is claimed is:

1. A glycidoxy group-containing organosilicon compound represented by formula (I)

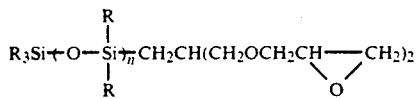

(1)

wherein R which may be the same or different each represents an alkyl group, an aryl group, or an alkenyl group, and n is 0 or an integer of 1 to 1,000.

2. A glycidoxy-group containing organosilicon compound as claimed in claim 1, wherein R is an alkyl group having 1 to 4 carbon atoms.

3. A glycidoxy-group containing organosilicon compound as claimed in claim 1, wherein R is methyl.

4. A glycidoxy-group containing organosilicon compound as claimed in claim 1, wherein n is an integer of 1 to 200.

* * * * *